United States Patent
Fang et al.

(10) Patent No.: US 10,301,348 B2
(45) Date of Patent: May 28, 2019

(54) COMPOUNDS FOR USE IN PREVENTION AND TREATMENT OF NEURODEGENERATIVE DISEASES AND PAIN

(71) Applicant: Academia Sinica, Taipei (TW)

(72) Inventors: Jim-Min Fang, Taipei (TW); Yun-Lian Lin, Taipei (TW); Jung-Hsin Lin, Taipei (TW); Chun-Jung Lin, Taipei (TW); Yijuang Chern, Taipei (TW); Nai-Kuei Huang, Taipei (TW); Hung-Li Wang, Taipei (TW); Benjamin Pang-hsien Tu, Taipei (TW); Chih-Cheng Chen, Taipei (TW)

(73) Assignee: ACADEMIA SINICA, Taipei (TW)

( * ) Notice: Subject to any disclaimer, the term of this patent is extended or adjusted under 35 U.S.C. 154(b) by 401 days.

(21) Appl. No.: 15/031,711

(22) PCT Filed: Oct. 22, 2014

(86) PCT No.: PCT/US2014/061734
§ 371 (c)(1),
(2) Date: Apr. 22, 2016

(87) PCT Pub. No.: WO2015/061426
PCT Pub. Date: Apr. 30, 2015

(65) Prior Publication Data
US 2016/0264613 A1    Sep. 15, 2016

Related U.S. Application Data (60) Provisional application No. 61/894,699, filed on Oct. 23, 2013.

(51) Int. Cl.
C07H 19/167     (2006.01)
C07H 19/16      (2006.01)
C07D 473/34     (2006.01)
A61K 31/7076    (2006.01)

(52) U.S. Cl.
CPC ......... *C07H 19/16* (2013.01); *A61K 31/7076* (2013.01); *C07D 473/34* (2013.01); *C07H 19/167* (2013.01); *Y02P 20/582* (2015.11)

(58) Field of Classification Search
None
See application file for complete search history.

(56) References Cited

U.S. PATENT DOCUMENTS

2012/0295863 A1   11/2012  Lin et al.

FOREIGN PATENT DOCUMENTS

| CN | 102740849 A    |   | 10/2012 |
|----|----------------|---|---------|
| WO | 88/03148 A2    |   | 5/1988  |
| WO | WO2011/069294  | * | 6/2011  |
| WO | WO 2011/069294 A1 |   | 6/2011 |
| WO | WO 2012/064340 A1 |   | 5/2012 |
| WO | 2013/120078 A1 |   | 8/2013  |
| WO | WO 2013/120078 A1 |   | 8/2013 |

OTHER PUBLICATIONS (5-Chlorothien-2-YL)Methylamine [online]. Chemical Book. 2008 [retrieved on Jan. 10, 2015]. Retrieved from the Internet: http://www.chemicalbook.com/ProductChemicalPropertiesCB3379451_EN.htm.

(5-Bromothien-2-YL)Methanol [online]. Chemical Book. 2010 [retrieved on Jan. 10, 2015]. Retrieved from the Internet: http://www.chemicalbook.com/ChemicalProductProperty_EN_CB0383668.htm.

Goncalves, et al., "Caffeine and Adenosine $A_{2A}$ Receptor Inactivation Decrease Striatal Neuropathology in a Lentiviral-Based Model of Machado-Joseph Disease," *Annals of Neurology*, vol. 73, No. 5, pp. 655-666 (2013).

Wang, et al., "$_D$- and $_L$-2',3'-Didehydro-2',3'-Dideoxy-3'-Fluoro-Carbocyclic Nucleosides: Synthesis, Anti-HIV Activity and Mechanism of Resistance," *Journal of Medicinal Chemistry*, vol. 50, No. 8, pp. 1828-1839 (2007).

International Search Report for International Application No. PCT/US14/61734 dated Jan. 23, 2015.

English translation of Chinese Office Action for Appl. No. 201480058727.3 dated Dec. 20, 2017.

Scarfati, S.R., et al, "Synthesis of 6-15N and 1-15N labeled adenosine monophosphates," Tetrahedron, Dec. 31, 1988, vol. 44, No. 20, pp. 6367-6372.

* cited by examiner

*Primary Examiner* — Traviss C McIntosh, III
(74) *Attorney, Agent, or Firm* — Birch, Stewart, Kolasch & Birch, LLP (57) ABSTRACT

Compounds for use in prevention and treatment of neurodegenerative disease and pain are disclosed. In one embodiment of the invention, the compound is selected from the group consisting of $N^6$-[(3-halothien-2-yl)methyl]adenosine, $N^6$-[(4-halothien-2-yl)methyl]adenosine, and $N^6$-[(5-halothien-2-yl)methyl]adenosine. In another embodiment of the invention, the compound is selected from the group consisting of $N^6$-[(2-bromothien-3-yl)methyl]adenosine, $N^6$-[(4-bromothien-3-yl)methyl]adenosine, $N^6$-[(5-bromothien-3-yl)methyl]adenosine, $N^6$-[(2-chlorothien-3-yl)methyl]adenosine, $N^6$-[(4-chlorothien-3-yl)methyl]adenosine, and $N^6$-[(5-chlorothien-3-yl)methyl]adenosine. Also disclosed are methods of making and using the same.

20 Claims, 4 Drawing Sheets
Specification includes a Sequence Listing.

FIG. 10A-1 ipsilateral site

FIG. 10A-2 contralateral

COMPOUNDS FOR USE IN PREVENTION AND TREATMENT OF NEURODEGENERATIVE DISEASES AND PAIN

CROSS-REFERENCE TO RELATED APPLICATIONS

This application is the U.S. National Stage Entry under § 371 of International Application No. PCT/US2014/061734, filed Oct. 22, 2014, which claims priority to U.S. Provisional Application No. 61/894,699, filed Oct. 23, 2013, each of which is incorporated in its entirety herein for all purposes.

FIELD OF THE INVENTION

The present invention relates to compounds for use in preventing and/or treating neurodegenerative diseases or pain, or both.

BACKGROUND OF THE INVENTION

United States patent publication No. US20120295863 discloses dual-action compounds targeting adenosine A2A receptor and adenosine transporter for prevention and treatment of neurodegenerative diseases. A selective $A_{2A}$ adenosine receptor ($A_{2A}R$) agonist named CGS21680 (in short, CGS) has been shown to be able to attenuate Huntington's disease (HD) symptoms in a transgenic mouse model, and rescue the urea cycle deficiency of HD disease by enhancing the activity of the ubiquitin-proteasome system (Chiang et al., 2009 *Hum Mol Genet.* 18:2929-2942; Chou et al., 2005 *J Neurochem.* 93:310-320). However, CGS is known to exert strong immunosuppressive effect and other side effects, and is therefore not suitable for clinical use.

$N^6$-(4-hydroxybenzyl)adenosine, designated as T1-11 in US20120295863 and also an $A_{2A}R$ agonist, has been suggested to have a therapeutic potential in treating neural degenerative diseases. However, it is still difficult to develop T1-11 as an orally available drug due to its poor bioavailability (F<5%). Oral bioavailability is an important property in drug development because it represents the percentage of a substance that reaches systemic circulation after absorption and metabolism.

SUMMARY OF THE INVENTION

In one aspect, the invention relates to a compound of formula (I) or (IA):

(I)

(IA)

or a pharmaceutically acceptable salt thereof, wherein X is halogen.

The halogen (F, Cl, Br or I) may be located at 3-, 4- or 5-position in formula (I), or at 2-, 4- or 5-position in formula (IA).

In one embodiment of the invention, the compound is selected from the group consisting of $N^6$-[(3-halothien-2-yl)methyl]adenosine, $N^6$-[(4-halothien-2-yl)methyl]adenosine, and $N^6$-[(5-halothien-2-yl)methyl]adenosine.

In another embodiment of the invention, the compound is selected from the group consisting of $N^6$-[(2-halothien-3-yl)methyl]adenosine, $N^6$-[(4-halothien-3-yl)methyl]adenosine, and $N^6$-[(5-halothien-3-yl)methyl]adenosine.

Further in another embodiment of the invention, the compound is selected from the group consisting of $N^6$-[(5-bromothien-2-yl)methyl]adenosine, $N^6$-[(4-bromothien-2-yl)methyl]adenosine, $N^6$-[(3-bromothien-2-yl)methyl]adenosine, $N^6$-[(5-chlorothien-2-yl)methyl]adenosine, $N^6$-[(4-chlorothien-2-yl)methyl]adenosine, and $N^6$-[(3-chlorothien-2-yl)methyl]adenosine.

In another embodiment of the invention, the compound is selected from the group consisting of $N^6$-[(2-bromothien-3-yl)methyl]adenosine, $N^6$-[(4-bromothien-3-yl)methyl]adenosine, $N^6$-[(5-bromothien-3-yl)methyl]adenosine $N^6$-[(2-chlorothien-3-yl)methyl]adenosine, $N^6$-[(4-chlorothien-3-yl)methyl]adenosine, and $N^6$-[(5-chlorothien-3-yl)methyl]adenosine.

In another aspect, the invention relates to a method for preparing the compound of formula (I) or formula (IA) as aforementioned, comprising the step of (I) or (II):

(I):
(a) reacting 6-chloropurine ribofuranoside in the presence of a base with (thienyl)methanamine that is substituted with fluorine, chlorine, bromine or iodine and has formula 3 or 3A:

(3)

(3A)

to afford the compound of formula (I) or (IA); or (II):
(a1) reacting (2',3'-O-isopropylidene)adenine in the presence of a base with a hydroxyl group-protecting agent to afford a derivative of (2',3'-O-isopropylidene)adenine having a hydroxyl protecting group;

(b) reacting the derivative of (2',3'-O-isopropylidene)adenine having the hydroxyl protecting group with an amine group-protecting agent to afford a derivative of (2',3'-O-isopropylidene)adenine having the hydroxyl protecting group and an amine protecting group;

(c) performing a coupling reaction by reacting the derivative of (2',3'-O-isopropylidene)adenine having the hydroxyl and amine protecting groups with a substituted (thienyl)methyl group-containing compound of formula 7 or 7A:

wherein X is F, Cl, Br, or I, and Y is X, OH, methanesulfonate ($OSO_2CH_3$, OMs), p-toluenesulfonate ($OSO_2C_6H_4$-p-$CH_3$, OTs), or trifluoromethanesulfonate ($OSO_2CF_3$, OTf), to afford a product containing the protecting groups and the substituted (thienyl)methyl group and; and (d) removing the protecting groups from the product of step (c) in an acidic condition to afford the compound of formula (I) or (IA).

In one embodiment of the invention, the base in step (a) may be diisopropylethylamine. The hydroxyl group-protecting agent may be tert-butyldimethylsilyl chloride. The amine group-protecting agent may be Di-tert-butyl dicarbonate. The base in step (a1) may be imidazole.

In another embodiment of the invention, in step (I)(a), the base is diisopropylethylamine and the substituted (thienyl)methanamine is: (i) (5-bromothien-2-yl)methanamine to afford V-[(5-bromothien-2-yl)methyl]adenosine; or (ii) (5-chlorothien-2-yl)methanamine to afford $1N^6$-[(5-chlorothien-2-yl)methyl]adenosine.

Further in another embodiment of the invention, the coupling reaction is preformed in the presence of triphenylphosphine and diisopropyl azodicarboxylate. The substituted (thienyl)methyl group-containing compound may be (5-bromothien-2-yl)methanol.

Further in another aspect, the invention relates to a composition comprising:

(a) a therapeutically effective amount of the compound as aforementioned or a pharmaceutically acceptable salt thereof, and (b) a pharmaceutically acceptable carrier, excipient or vehicle.

Yet in another aspect, the invention relates to use of the compound as aforementioned in the manufacture of a medicament for treating a neurodegenerative disease and/or pain in a subject in need thereof. Alternatively, the invention relates to the compound as aforementioned for use in treating a neurodegenerative disease and/or pain in a subject in need thereof. The neurodegenerative disease may be a protein-misfolding disease.

In one embodiment of the invention, the neurodegenerative disease is selected from the group consisting of Alzheimer's disease, Parkinson's disease, amyotrophic lateral sclerosis, Prion disease, Huntington's disease, and spinal cerebellar ataxias. The spinal cerebellar ataxias may be selected from the group consisting of spinal cerebellar ataxias 2, spinal cerebellar ataxias 3, and spinal cerebellar ataxias 7. The pain may be acid-induced pain. The acid-induced pain may be acid-induced muscle pain. The acid-induced muscle pain may be acid-induced chronic muscle pain.

In one embodiment of the invention, the pain is selected from the group consisting of inflammatory pain, cancer pain, chest pain, back pain, neck pain, shoulder pain, migraine, headache, myofascial pain, join pain, muscular pain syndromes, neuropathic pain, peripheral pain, sympathetic pain, postoperative pain, post-traumatic pain, and multiple sclerosis pain.

In another embodiment of the invention, the pain may be a dysfunctional pain. The dysfunctional pain may be selected from the group consisting of fibromyalgia, myofascial pain, bladder pain syndrome, and a pain caused by irritable bowel syndrome.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 5A-C show that T1-11 ameliorates the motor dysfunction and pontine neuronal death of SCA3 transgenic mice. (A) SCA3 transgenic mice were given drinking water containing vehicle (0.2% DMSO) or T1-11 (0.1 mg/ml) beginning at 4 weeks-old. Rotarod test showed that compared to wild-type (WT) mice, vehicle-treated 4-month-old ataxin-3-Q79 transgenic mice exhibited a significantly shorter latency to fall and motor incoordination. Rotarod performance of T1-11-treated 4-month-old SCA3 transgenic mice (1 mg per day) was significantly better than that of vehicle-treated ataxin-3-Q79 mice at the same age. Each point shows the mean±S.E. of 7-8 mice. (B-C) Immunohistochemical staining of neuronal marker NeuN indicated that daily oral administration of T1-11(1 mg per day) significantly ameliorated neuronal death in the pontine nuclei of a SCA3 transgenic mouse at the age of 4 months (SCA3+T1-11). Scale bar is 50 µm. Each bar shows the mean±S.E. of 7-8 mice. * P<0.01 compared to SAC3 transgenic mice.

DETAILED DESCRIPTION OF THE INVENTION

Definitions

Unless otherwise defined, all technical and scientific terms used herein have the same meaning as commonly understood by one of ordinary skill in the art to which this invention pertains. In the case of conflict, the present document, including definitions will control.

The term "treating" or "treatment" refers to administration of an effective amount of a therapeutic agent to a subject in need thereof, who has a neurodegenerative disease and/or pain, or a symptom or predisposition toward such a disease and/or pain, with the purpose of cure, alleviate, relieve, remedy, ameliorate, or prevent the disease and/or pain, the symptoms of it, or the predisposition towards it. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by calculations from the following formula:

$$HED = \text{animal dose in mg/kg} \times (\text{animal weight in kg/human weight in kg})^{0.33}.$$

JMF 1907 denotes the compound $N^6$-[2-(indol-3-yl)ethyl] adenosine and was disclosed in U.S. patent publication No. 20120295863 A1 as compound 6.

Chemical Synthesis

In one approach, 6-chloropurine ribofuranoside (2) was treated with an optionally substituted (thienyl)methanamine (3) in the presence of a base to give the desired compound of formula (I).

For example, diisopropylethylamine was used as a base, and the substitution reaction of 6-chloropurine ribofuranoside with (5-bromothien-2-yl)methanamine was carried out by heating in a solvent of 1-propanol to afford $N^6$-[(5-bromothien-2-yl)methyl]adenosine (JMF3464, structure 1).

7

Scheme 1

8

Scheme 2

In another approach, (2′,3′-O-isopropylidene)adenine (4) was treated with tert-butyldimethylsilyl chloride (TBDM-

SCl) in the presence of a base imidazole to give a silyl ether derivative (5). The 6-amino group was protected as a carbamate 6 bearing tert-butoxycarbonyl (Boc) substituent. An optionally substituted (thienyl)methyl group was introduced, and the desired compound of formula (I) was obtained after removal of all protecting groups in acidic conditions.

For example, the coupling reaction of compound 6 with (5-bromothien-2-yl)methanol (compound 7, wherein X=5-Br, Y=OH) was promoted by using triphenylphosphine and diisopropyl azodicarboxylate (DIAD) to give compound 8. Global deprotection of the silyl, acetonide and Boc groups in compound 8 was achieved in acidic conditions to give compound 1.

Using the same chemical approach, compound (IA), was obtained.

Scheme 3

X = F, Cl, Br, I
Y = X, OH, OMs, OTs, OTf

8A (IA)

Oral Bioavailability

Figure 1A:
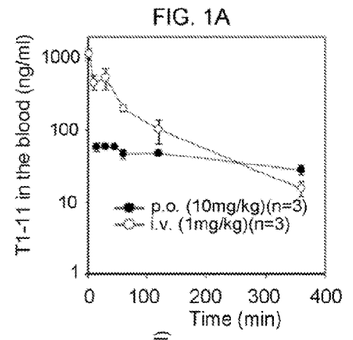
FIG. 1 shows the blood concentrations of T1-11 (A) and JMF3464 (B) in ICR mice receiving intravenous (1 mg/kg) or oral (10 mg/kg) of T1-11 or JMF3464. The oral bioavailability of T1-11 and JMF3464 were estimated to be 2.8% and 17.4%, respectively.
Figure 1B:
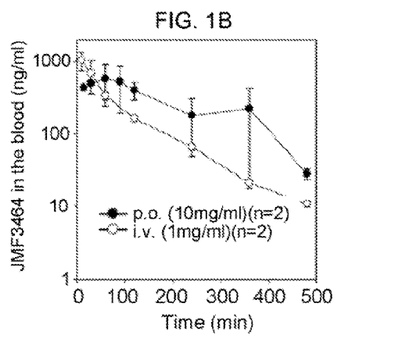

To measure oral bioavailability of a test compound, blood samples were collected from male ICR mice (6 weeks old; 20-25 g) after oral (10 mg/kg) or intravenous (1 mg/kg) administrations of the test compound. The blood samples collected at the indicated periods were extracted with methanol containing 0.1% formic acid, and then 10 μL of each extracted sample were injected to UPLC-MSMS for quantitation. The results (FIG. 1A-B) showed that oral bioavailability of T1-11 and JMF34964 in ICR mice were 2.8% and 17.4%, respectively, indicating that the oral absorption of JMF3464 was more than 6-fold higher than that of T1-11.

JMF3464 Binding to $A_{2A}R$ and ENT1 and Protecting Neuronal Cell Apoptosis

Figure 2:
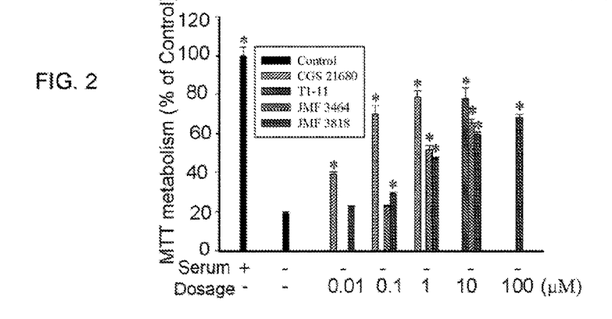
FIG. 2 shows the effects of $A_{2A}R$ agonists (CGS21680, T1-11, JMF3464, and JMF3818) on serum deprivation-induced cell death. Serum-deprived PC12 cells were treated with or without the indicated reagent(s) for 24 h. Cell viability was expressed as a percentage of the results from MTT assays compared to the mean of a serum-containing control group. Data points represent the mean±SEM (n=3~6).

We first characterized the pharmacological properties of JMF3464 using radioligand binding assays. Table 1 shows pharmacological properties of T1-11, JMF1907, and JMF3464. Binding of the indicated compounds to $A_{2A}$ adenosine receptor ($A_{2A}R$) and an adenosine transporter (ENT1) was characterized using standard binding protocols. As shown in Table 1, JMF3464 bound to the $A_{2A}R$ and an adenosine transporter—equilibrative nucleoside transporter 1. The affinity of JMF3464 toward $A_{2A}R$ was similar to those of T1-11 and JMF1907 (an analogue of T1-11), whereas its affinity toward ENT1 was much better than those of T1-11 and JMF1907. Our study also indicated that $N^6$-[(5-chlorothien-2-yl)methyl]adenosine (JMF3818) also inhibited the apoptosis of PC12 cells caused by serum withdrawal. JMF3818 at 10 μM inhibited $A_{2A}$ receptor and adenosine transporter (ENT1) by 54% and 96%, respectively (FIG. 2).

TABLE 1

| Compound | $A_{2A}R$ (Ki, µM) | ENT1 (Ki, µM) |
|---|---|---|
| CGS21680 | 0.08 | — |
| T1-11 | 2.62 | 0.54 |
| JMF1907 | 4.39 | 3.47 |
| JMF3464 | 1.70 | 0.05 |

Figure 3A:
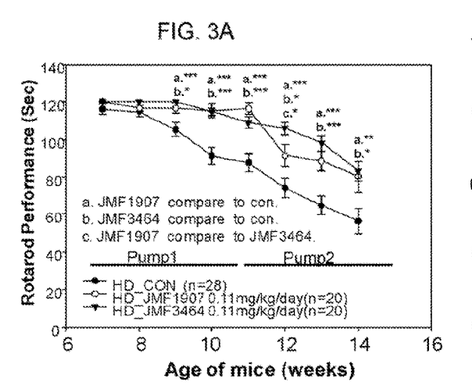
FIGS. 3A-B show the effect of JMF3464 on motor deficits and lifespan. JMF3464 (0.11 µg/mouse/day), JMF1907 (0.11 µg/mouse/day) or vehicle (CON) was administrated subcutaneously to the indicated mice of 7 weeks old using ALZET osmotic minipumps for 6 weeks. Rotarod performance (A) and lifespan (B) of these mice were assessed. * p<0.05. *** p<0.005.
Figure 3B:
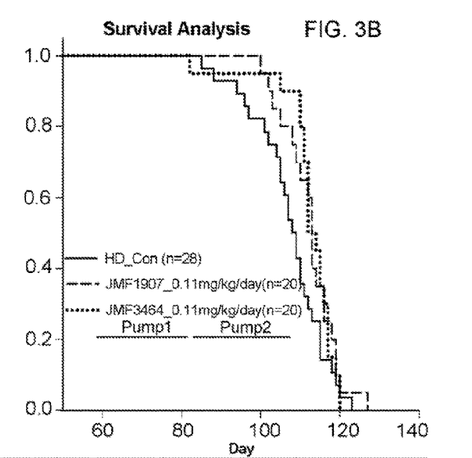

JMF3464 Exerting Beneficial Effects on Major Symptoms of Huntington's Disease (HD) in a Transgenic Mouse Model of HD As the $A_{2A}R$ and ENT1 are located in the striatum and have been implicated in striatal function, we hypothesized that chronic treatment with JMF3464 would modulate the progression of HD. We tested the effect of JMF3464 in a transgenic mouse model (R6/2) of HD in which $A_{2A}R$ agonists have beneficial effects. The addition of JMF3464 (0.11 mg/kg/day) to mice from the age of 7 weeks counteracted the progressive deterioration in motor coordination as assessed by rotarod performance (FIG. 3A). The shortened lifespan of R6/2 mic was also improved by a sustained (long term) treatment with JMF3464.

Beneficial Effects of JMF3464 on Spinal Cerebellar Ataxias 2 (SCA2)

Figure 4A:
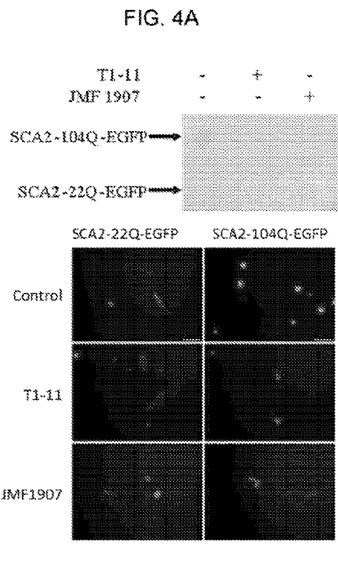
FIGS. 4A-B show the effects of T1-11 in preventing mutant SCA2 gene overexpression-induced protein aggregations and behavioral performance in SCA2 transgenic mice. (A) pSCA2-22Q-EGFP or pSCA2-104Q-EGFP-transfected cells were treated with 10 µM T1-11 or 10 µM JMF1907 (a T1-11-derived $A_{2A}$-R agonist) for 24 h. Cells were harvested and subjected to a filter retardation assay or image acquisition. (B) Wild type (WT) or transgenic mice (SCA2) drank water with or without T1-11. Rotarod performance was used to measure the behavioral function of mice.
Figure 4B:
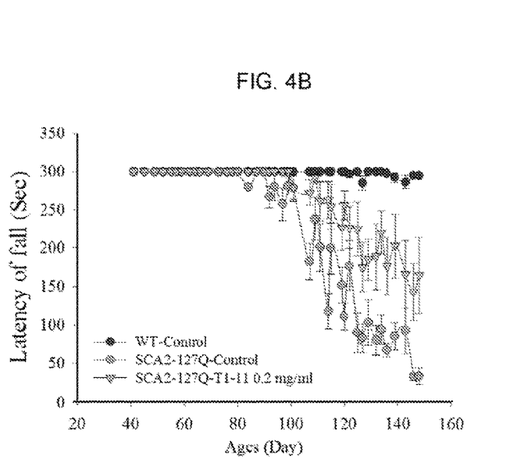

Since activating proteasome activity could be the mechanism of $A_{2A}R$ receptor signaling pathway in preventing mutant Htt aggregations or behavioral performance in R6/2 transgenic mouse (Huang et al., 2011 *PLoS One*. 6:e20934; Lee et al., 2012 *PLoS One*. 7:e38865), it is possible that $A_{2A}R$ agonist might also have benefits in alleviating other polyQ diseases, such as SCA2. Indeed, our data showed that T1-11 is effective is preventing mutant ATXN2 aggregations (FIG. 4A) and behavioral performance in SCA2 transgenic mice (ATAXN2$^{Q127}$) (FIG. 4B), supporting the above hypothesis. Given that the bioavailability of JMF3464 is significantly better than T1-11, we reasoned that JMF3464 would also produce a beneficial effect on SCA2.

Beneficial Effects of T1-11 and its Analogues on Spinocerebellar Ataxias 3 (SCA3)

Figure 5A:
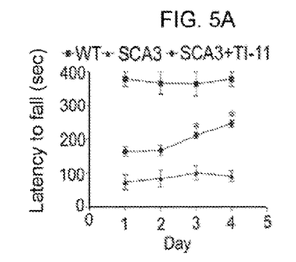
Figure 5B:
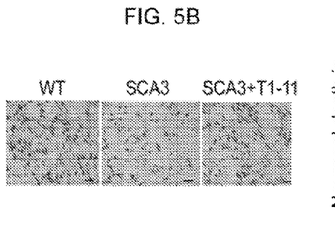
Figure 5C:
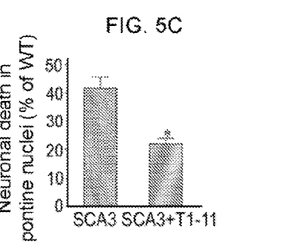
Figure 6A:
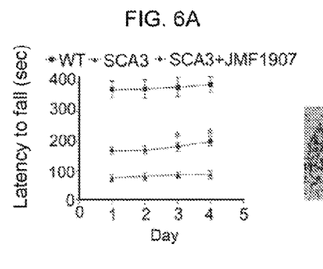
FIGS. 6A-C show that JMF1907 alleviates the ataxic symptom and pontine neuronal death of SCA3 transgenic mice. (A) Rotarod test indicated that compared to vehicle-treated 4-month-old SCA3 transgenic mice, rotarod performance of JMF1907-treated 4-month-old SCA3 mice (1 mg per day) was significantly improved. Each point shows the mean±S. E. of 6 mice. (B-C) Immunocytochemical staining of NeuN showed that oral administration of JMF1907 (1 mg per day) significantly prevented neuronal death in the pontine nuclei of a SCA3 mouse at the age of 4 months (SCA3+JMF1907). Scale bar is 50 µm. Each bar represents the mean±S.E. of 6 mice. * P<0.01 compared to SCA3 mice.
Figure 6B:
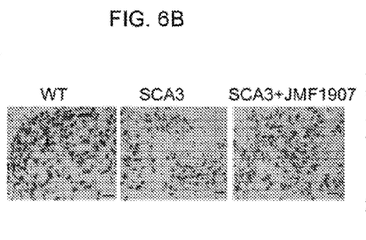
Figure 6C:
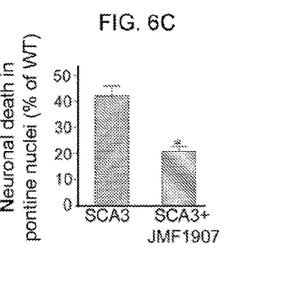

Compared to wild-type mice, vehicle-treated SCA3 transgenic mice expressing polyglutamine-expanded ataxin-3-Q79 displayed various ataxic symptoms, including an impaired rotarod performance (FIGS. 5A and 6A) with an onset age of about 3-4 months. As shown in FIGS. 5A and 6A, 4 month-old SCA3 transgenic mice treated with daily oral administration of T1-11 (1 mg per day) or JMF1907 (1 mg per day) exhibited a significantly improved rotarod performance. Similar to SCA3 patients, a prominent neuronal death was found in the pontine nuclei of SCA3 transgenic mice (FIGS. 5B and 6B). In accordance with the results of rotarod assays, daily oral treatment of T1-11 (FIGS. 5B and 5C) or JMF1907 (FIG. 6B and FIG. 6C) significantly alleviated pontine neuronal death in SCA3 transgenic mice (FIGS. 5B, 5C, 6B and FIG. 6C). The results provide evidence that a sustained oral treatment of T1-11 or JMF1907 ameliorates neurological and neuropathological phenotypes of SCA3 transgenic mice.

Figure 7A:
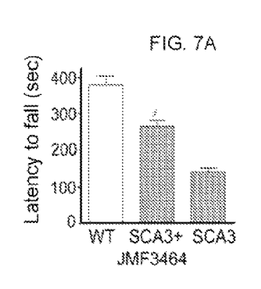
FIGS. 7A-C show that JMF3464 ameliorates the ataxia and pontine neuronal death of SCA3 transgenic mice. (A) SCA3 transgenic mice displayed an impaired rotarod performance. Daily administration of JMF3464 (0.3 mg per day) greatly improved the rotarod performance of 4-month-old SCA3 mice. (B-C) Immunocytochemical staining of neuronal marker NeuN demonstrated that daily oral treatment of JMF3464 (0.3 mg per day) significantly ameliorated neuronal death in the pontine nuclei of a SCA3 transgenic mouse at the age of 4 months. Each bar shows the mean±S.E. of 6 mice. #P<0.01 compared to SCA3 transgenic mice.
Figure 7B:
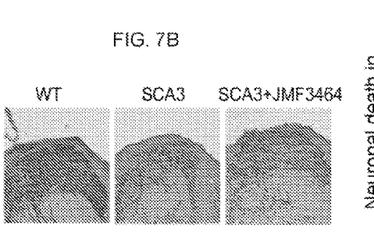
Figure 7C:
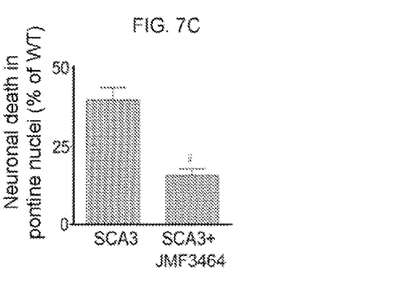

JMF3464 has a much higher bioavailability. Therefore, JMF3464 was also expected to exert a beneficial effect on mutant ataxin-3-Q79-induced ataxia and neurodegeneration in SCA3 transgenic mice. As expected, daily application of JMF3464 (0.3 mg per day) alleviated the ataxia (FIG. 7A) and pontine neuronal death (FIGS. 7B and 7C) of SCA3 transgenic mice.

Beneficial Effects of JMF1907 and JMF3464 on Amyotrophic Lateral Sclerosis (ALS)

Figure 8A:
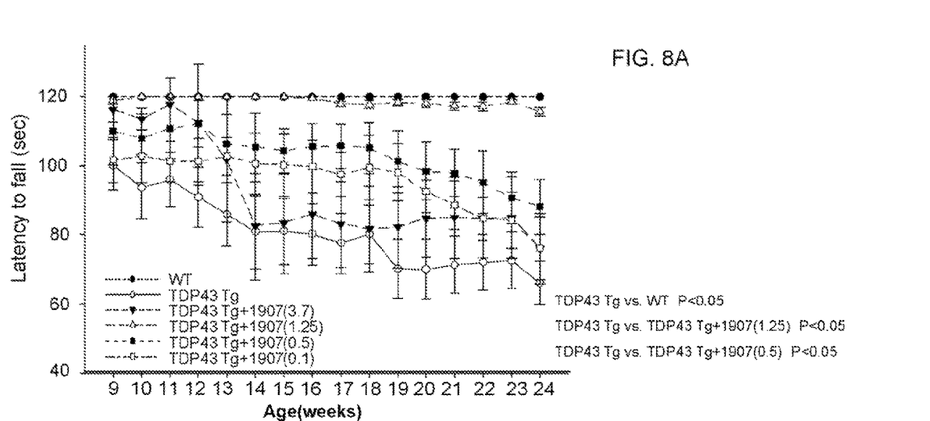
FIGS. 8A-B show that treatment with JMF1907 improved the motor functions of the TDP-43 transgenic mice. 4 different doses of JMF1907 (3.7, 1.25, 0.5, 0.1 mg/kg) were tested. CTL: transgenic mice treated with DMSO. WT: wild type mice treated with DMSO. Statistics was done with two-way ANOVA. For the Rotarod, statistical significance was reached at all points for 1.5 & 0.5 mg/kg, from 12-21 wk for 0.1 mg/kg, and 10-12 wk for 3.7 mg/kg. For grip strength, statistical significance was reached at all points for all tested doses. N=18 (CTL), 15 (WT), 15 (0.1), 15 (0.5), 15 (1.25), 5 (3.7).
Figure 8B:
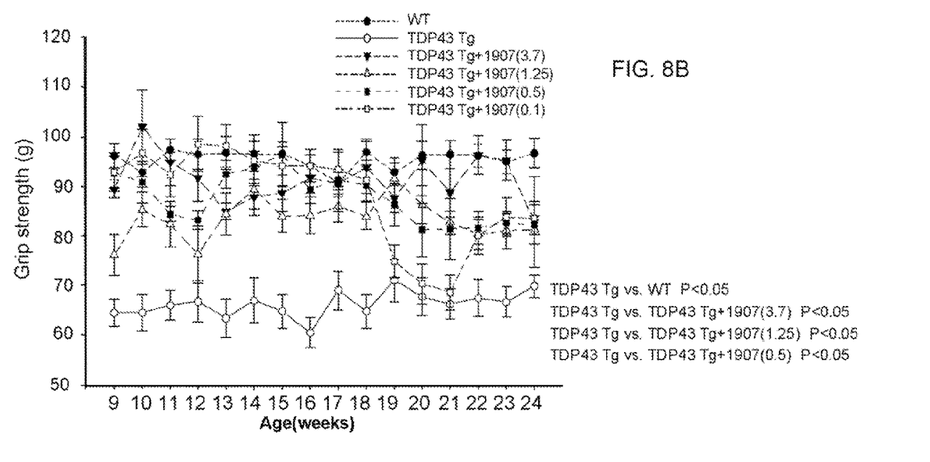
Figure 9:
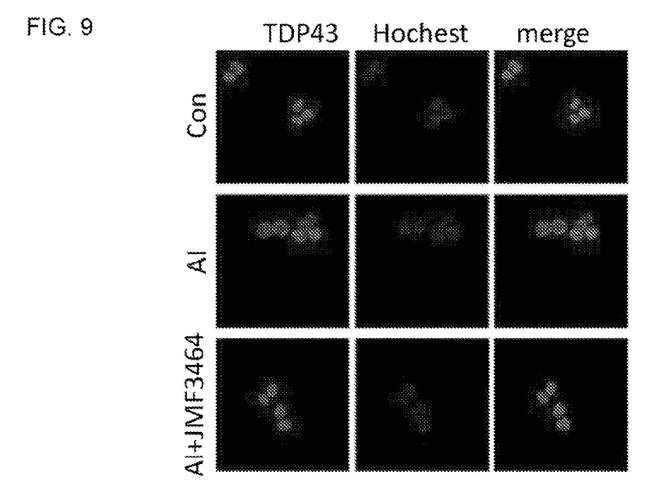
FIG. 9 show treatment with JMF3464 reduced TDP-43 mislocalization in NSC34 cells. Cells were pretreated with JMF3464 (30 µM) for one hour, and then treated with AICAR (1 mM, AI) in the presence of JMF3464 for additional 24 hrs. TDP-43 (red) localization was analysed by immunostaining. The locations of nuclei were marked by Hochest (blue).

As shown in FIG. 8A-B, transgenic mice given JMF1907 at 4 different doses (3.7, 1.25, 0.5 and 0.1 mg/kg/day) performed significantly better on rotarod and grip strength tests than control mice. The dose of 1.25 mg/kg showed the greatest benefit. These data indicated a clear improvement on the motor function. JMF3464, an analogue of T1-11 and JMF1907, has a much higher bioavailability. Therefore, JMF3464 is expected to exert a beneficial effect in ALS mice. Treating NSC34 cells with JMF3464 normalized TDP-43 mislocalization caused by AMPK activation (FIG. 9), which supports the notion that JMF3464 is capable of preventing the initial step of ALS pathogenesis. These findings support that JMF3464 exhibits beneficial effects on ALS.

Beneficial Effects of JMF3464 on Pain

Figure 10A:
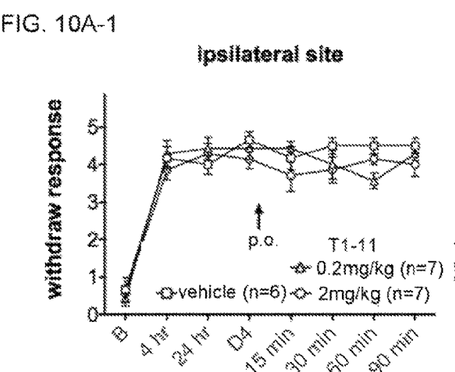
FIGS. 10A-C show the analgesic effect of JMF3464 on a mouse model of fibromyalgia. (A-1 and A-2) Oral administration of T1-11 showed no analgesic effect on a mouse model of fibromyalgia, in which mice developed chronic muscle pain after intramuscular acid injection and a genistein treatment. Open arrows indicate the time mice received acid injection. Black arrows indicate the time mice received T1-11 (p.o.). (B) JMF3464 shows an analgesic effect on a mouse model of fibromyalgia, in which mice developed chronic widespread pain after treated with intermittent cold stress for 2 days. The analgesic effect of JMF3464 is dose-dependent. The effective dose started from 100 µg/kg (i.p.). (C) Oral administration of JMF3464 (1 mg/kg) showed an analgesic effect on the intermittent cold stress model.
Figure 10A:
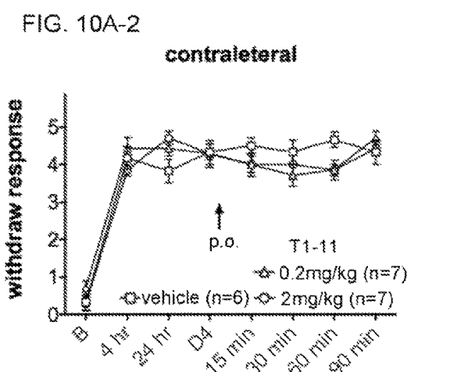
Figure 10B:
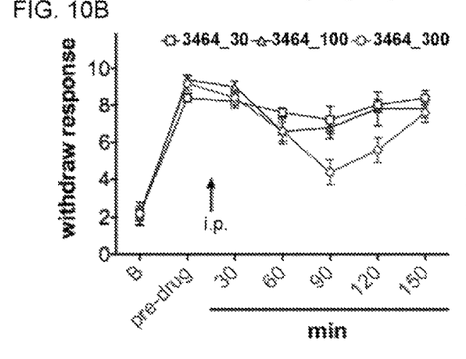
Figure 10C:
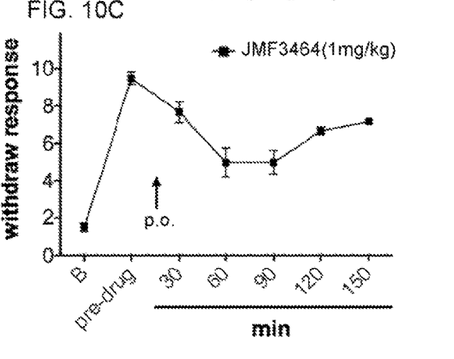

Although T1-11 (i.p.) showed excellent analgesic effects on 2 mouse models of fibromyalgia (acid-induced chronic widespread pain and intermittent cold stress models), its bioavailability is very low. Oral administration of T1-11 (up to 2 mg/kg) showed no analgesic effect on an acid-induced chronic widespread pain model, in which mice developed fibromyalgia-like pain after intramuscular acid injection and a genistein treatment (FIG. 10A). JMF3464, an analogue of T1-11, showed an analgesic effect on a mouse model of fibromyalgia, in which mice developed chronic widespread pain after being treated with an intermittent cold stress for 2 days (FIG. 10B). Consistent with its good bioavailability, oral administration of JMF3464 (1 mg/kg) showed an analgesic effect on the intermittent cold stress model (FIG. 10C).

EXAMPLE 1

All reagents and solvents were of reagents grade and were used without further purification unless otherwise specified. Tetrahydrofuran and diethyl ether were distilled from Na/benzophenone and $CH_2Cl_2$ was distilled from $CaH_2$. All air or moisture sensitive experiments were performed under argon. All glasses were dried in an oven for more than 2 hours and used after cooling to room temperature in desiccators. Microwave reactions were conducted using a focused single mode microwave unit (CEM Discover). The machine consists of a continuously focused microwave power delivery system with operator-selectable power output.

Melting points were recorded on a Yanaco micro apparatus. Optical rotations were measured on digital polarimeter of Japan JASCO Co. DIP-1000. $[\alpha]_D$ values are given in units of $10^{-1}$ deg $cm^2$ $g^{-1}$. Infrared (IR) spectra were recorded on Nicolet Magna 550-II. NMR spectra were obtained on Varian Unity Plus-400 (400 MHz) and chemical shifts (δ) were recorded in parts per million (ppm) relative to $\delta_H$ 7.24/$\delta_C$ 77.0 (central line of t) for $CHCl_3/CDCl_3$, $\delta_H$ 2.05/$\delta_C$ 29.92 for $(CH_3)_2CO/(CD_3)_2CO$, $\delta_H$ 3.31/$\delta_C$ 49.0 for $CH_3OH/CD_3OD$, and $\delta_H$ 2.49 (m)/$\delta_C$ 39.5 (m) for $(CH_3)_2SO/(CD_3)_2SO$. The splitting patterns are reported as s (singlet), d (doublet), t (triplet), q (quartet), m (multiplet) and br (broad). Coupling constants (J) are given in Hz. The ESI-MS experiments were conducted on a Bruker Daltonics BioTOF III high-resolution mass spectrometer. Analytical thin-layer chromatography (TLC) was performed on E. Merck silica gel 60 $F_{254}$ plates (0.25 mm). Compounds were visualized by UV, anisaldehyde or ninhydrin spray. Column chromatography was carried out on columns packed with 70-230 mesh silica gel.

Purity of compounds was assessed to be ≥95% by HPLC (Agilent HP-1100) with detection at 280 nm wavelength.

2',3'-O-Isopropylidene-5'-O-(tert-butyldimethylsilyl)adenosine (5)

To a solution of 2',3'-(O-isopropylidene)adenosine (4, 614 mg, 2.00 mmol) and imidazole (408 mg, 6 mmol) in anhydrous $CH_2Cl_2$ (12 mL), cooled in an ice bath, was added tert-butyldimethylsilyl chloride (TBDMSCl, 452 mg, 3 mmol) at 0° C. under an atmosphere of $N_2$. The ice bath was removed, and the mixture was stirred for 12 h at room temperature. Methanol (4 mL) was added, and the mixture was stirred for another 15 min, and then concentrated under reduced pressure by rotary evaporation. The solid residue was dissolved in $CH_2Cl_2$, and washed successively with 1 M HCl, deionized water and brine. The organic layer was collected, dried over $MgSO_4$, and filtered. The filtrate was concentrated under reduced pressure to give compound 5 (819 mg, 1.57 mmol, 78% yield) as white solids.

6-N-tert-Butoxycarbonyl-2',3'-O-isopropylidene-5'-O-(tert-butyldimethylsilyl)adenosine (6)

A solution of compound 5 (819 mg, 1.57 mmol) and 4-(dimethylamino)pyridine (DMAP, catalytic amount) in anhydrous THF (10 mL) was stirred for 2 min under $N_2$. The solution was cooled in an ice bath, and di-tert-butyl dicarbonate ($(Boc)_2O$, 1.08 mL, 4.71 mmol) was added dropwise. The ice bath was removed, and the mixture was stirred for 12 h at room temperature. After the reaction completed, the mixture was concentrated under reduced pressure by rotary evaporation. The crude product was dissolved in $CH_2Cl_2$, and washed successfully with 1 M HCl, deionized water and brine. The organic layer was collected, dried over $MgSO_4$, and filtered. The filtrate was concentrated under reduced pressure to give a bis-Boc compound (859 mg, 1.38 mmol, 87% yield) as pale yellow foam.

To a solution of bis-Boc compound (400 mg, 0.64 mmol) in methanol (8 mL) was added methylamine (0.25 mL of 40% solution in methanol, 2.54 mmol). The mixture was stirred at room temperature for 20 h until the TLC analysis showed complete consumption of the starting material. The mixture was concentrated under reduced pressure by rotary evaporation. The crude product was purified by chromatography on a silica gel column with elution of EtOAc/hexane (0:1 to 2:1 gradients) to give compound 6 (300 mg, 0.57 mmol, 88% yield) as pale yellow oil.

6-N-(5-Bromothien-2-yl)methyl-6-N-tert-butoxycarbonyl-2',3'-O-isopropylidene-5'-O-(tert-butyldimethylsilyl)adenosine (8, X=5-Br)

A solution of compound 6 (300 mg, 0.57 mmol), (5-bromothien-2-yl)methanol (164 mg, 0.85 mmol) and triphenylphosphine (226 mg, 0.85 mmol) in anhydrous THF (9 mL) was stirred at 45° C. for 2 min under an atmosphere of $N_2$. Diisopropyl azodicarboxylate (DIAD, 0.168 mL, 0.85 mmol) was added dropwise. The mixture was stirred for another 45 min until the TLC analysis showed disappearance of compound 6. The mixture was concentrated under reduced pressure by rotary evaporation. The crude product was purified by flash chromatography (EtOAc/hexane=1:9) to give compound 8 (X=5-Br) as pale yellow oil.

$N^6$-[(5-Bromothien-2-yl)methyl]adenosine (JMF3464)

Method A: A suspension of compound 8 (X=5-Br, 138 mg, 0.19 mmol) in deionized water (5 mL) and THF (1 mL) was stirred and cooled in an ice bath. Trifluoroactetic acid (5 mL) was added dropwise at 0° C. The mixture was stirred for 10 min, the ice bath was removed, and the mixture was stirred for another 30 min. The mixture was concentrated under reduced pressure by rotary evaporation. The crude product was purified by flash chromatography (MeOH/EtOAc=1:49) to give JMF3464 (compound 1) as white powder.

Method B: A mixture of (S-bromothien-2-yl)methanamine (768 mg, 4 mmol), 6-chloropurine ribofuranoside (143 mg, 0.5 mmol), and diisopropylethylamine (2 mL, 12 mmol) in 1-propanol (20 mL) was heated at 70° C. for 7 h. The mixture containing the desired product and unreacted (5-bromothien-2-yl)methanamine was treated with di-tert-butyl dicarbonate (0.92 mL, 4 mmol) in THF (6 mL) and $NaHCO_3$ (672 mg, 8 mmol) at room temperature for 2 h. The mixture was concentrated by rotary evaporation, and purified by flash chromatography (silica gel, MeOH/EtOAc=1:9). The desired product JMF3464 (59 mg, 27% yield) was obtained by recrystallization from MeOH. The purity of product was 96% as shown by HPLC on an HC-C18 column (Agilent, 4.6×250 mm, 5 μm) with elution of gradients of 50% aqueous MeOH.

Method C: In a sealed tube (15 mL) were added (S-bromothien-2-yl)methanamine (384 mg, 2 mmol), 6-chloropurine ribofuranoside (287 mg, 1 mmol), and diisopropylethylamine (3 mL, 17 mmol) in EtOH (8 mL). The sealed tube was placed into the cavity of a focused monomode microwave reactor (CEM Discover) and irradiated in 100 W for 20 min at 80° C. The solvent was removed by rotary evaporation. The residue was purified by flash chromatography (silica gel, MeOH/EtOAc=1:9), and recrystallized from MeOH to afford the desired product JMF3464 (159 mg, 36% yield).

$C_{15}H_{16}BrN_5O_4S$; yellow powder; mp 141.4-141.7° C.; $[\alpha]^{25}_D=-43.0$ (DMSO, c=1.0); TLC (2-propanol/hexane (2:3)) $R_f=0.38$; $^1H$ NMR (DMSO-$d_6$, 400 MHz) δ 8.55 (1 H, br s), 8.40 (1 H, s), 8.29 (1 H, br s), 7.03 (1 H, d, J=3.6 Hz), 6.78 (1 H, d, J=4.0 Hz), 5.90 (1 H, d, J=6.0 Hz), 5.45 (1 H, d, J=6.0 Hz), 5.34-5.32 (1 H, m), 5.19 (1 H, d, J=4.4 Hz), 4.76 (2 H, s), 4.63-4.59 (1 H, m), 4.15-4.14 (1 H, m), 3.96-3.95 (1 H, m), 3.69-3.65 (1 H, m), 3.57-3.52 (1 H, m), $^{13}C$ NMR (DMSO-$d_6$, 100 MHz) δ 153.9, 152.2, 148.5, 145.0, 140.2, 129.6, 126.3, 120.0, 109.7, 87.9, 85.8, 73.5, 70.6, 61.6, 42.9, ESI-MS calcd for $C_{15}H_{17}BrN_5O_4S$: 442.0185, found: m/z 442.0189 $[M+H]^+$.

$N^6$-(Thien-3-yl-methyl)adenosine (JMF3461)

A mixture of 3-(aminomethyl)thiophene (0.25 mL, 2.5 mmol), 6-chloropurine ribofuranoside (143 mg, 0.5 mmol), and diisopropylethylamine (2 mL, 12 mmol) in 1-propanol (25 mL) was heated at 80° C. for 6 h. The mixture was concentrated by rotary evaporation, and recrystallized from MeOH to yield the desired product JMF3461 (136 mg, 75% yield). The purity of product was 99% as shown by HPLC on an HC-C18 column (Agilent, 4.6×250 mm, 5 μm) with elution of gradients of 50% aqueous MeOH. $C_{15}H_{17}N_5O_4S$; yellow powder; mp 134.3-135.1° C.; $[\alpha]^{24}_D=-58.6$ (DMSO, c=1.0); TLC (2-propanol/hexane, (2:3)) $R_f=0.33$; $^1H$ NMR (DMSO-$d_6$, 400 MHz) δ 8.36 (2 H, br s), 8.22 (1 H, s), 7.43 (1 H, dd, J=3, 5 Hz), 7.28 (1 H, d, J=1.6 Hz), 7.09 (1 H, d, J=4.8 Hz), 5.88 (1 H, d, J=6.4 Hz), 5.43 (1 H, d, J=6.0 Hz), 5.38 (1 H, q, J=4.6 Hz), 5.17 (1 H, d, J=4.4 Hz), 4.69 (2 H, s), 4.63-4.16 (1 H, m), 4.14-4.13 (1 H, m), 3.97-3.95 (1 H, m), 3.69-3.64 (1 H, m), 3.57-3.52 (1 H, m), $^{13}C$ NMR (DMSO-$d_6$, 100 MHz) δ 154.4, 152.3, 148.5, 140.8, 139.9, 127.9, 125.1, 120.0, 119.8, 87.9, 85.9, 73.5, 70.7, 61.7, 42.9; ESI-MS calcd for $C_{15}H_{18}N_5O_4S$: 364.1080, found: m/z 364.1079 $[M+H]^+$.

$N^6$-(Thien-2-yl-methyl)adenosine (JMF3462)

A mixture of 2-(aminomethyl)thiophene (0.25 mL, 2.5 mmol), 6-chloropurine ribofuranoside (143 mg, 0.5 mmol), and diisopropylethylamine (2 mL, 12 mmol) in 1-propanol (25 mL) was heated at 80° C. for 7 h. The mixture was concentrated by rotary evaporation, and recrystallized from MeOH to yield the desired product JMF3462 (154 mg, 85% yield). The purity of product was 99% as shown by HPLC on an HC-C18 column (Agilent, 4.6×250 mm, 5 μm) with elution of gradients of 50% aqueous MeOH. $C_{15}H_{17}N_5O_4S$; white powder; mp 149.2-149.7° C.; $[\alpha]^{25}_D$ –68.2 (DMSO, c=1.0); TLC (2-propanol/hexane, (2:3)) $R_f$=0.35; $^1H$ NMR (DMSO-$d_6$, 400 MHz) δ 8.51 (1 H, br s), 8.39 (1 H, s), 8.27 (1 H, br s), 7.32 (1 H, d, J=5.2 Hz), 7.28 (1 H, d, J=3.2 Hz), 6.93 (1 H, dd, J=1.8, 2.6 Hz), 5.89 (1 H, d, J=6.0 Hz), 5.46-5.45 (1 H, m), 5.36 (1 H, q, J=4.6 Hz), 5.20-5.18 (1 H, m), 4.64 (2 H, s), 4.16-4.13 (1 H, m), 3.97-3.95 (1 H, m), 3.70-3.65 (1 H, m), 3.58-3.52 (1 H, m), 3.57-3.52 (1 H, m), $^{13}C$ NMR (DMSO-$d_6$, 100 MHz) δ 154.1, 152.2, 148.5, 142.9, 140.0, 126.5, 125.3, 124.7, 120.0, 87.9, 85.9, 73.5, 70.6, 61.6, 42.9; ESI-MS calcd for $C_{15}H_{18}N_5O_4S$: 364.1080, found: m/z 364.1081 $[M+H]^+$.

$N^6$-[(4-Bromothien-2-yl)methyl]adenosine

A mixture of (4-bromothien-2-yl)methanamine (1152 mg, 6 mmol), 6-chloropurine ribofuranoside (214 mg, 0.75 mmol), and diisopropylethylamine (3 mL, 18 mmol) in 1-propanol (30 mL) was heated at 70° C. for 7 h. The mixture containing the desired product and unreacted (3-bromothien-2-yl)methanamine was treated with di-tert-butyl dicarbonate (1.4 mL, 6 mmol) in THF (8 mL) and NaHCO$_3$ (1 g, 1.2 mmol) at room temperature for 2 h. The mixture was concentrated by rotary evaporation and purified by flash chromatography (silica gel, MeOH/EtOAc=1:9) to afford $N^6$-[(4-bromothien-2-yl)methyl]adenosine.

$N^6$-[(3-Bromothien-2-yl)methyl]adenosine

In a sealed tube (15 mL) was added (3-bromothien-2-yl) methanamine (576 mg, 3 mmol), 6-chloropurine ribofuranoside (430 mg, 1.5 mmol), and diisopropylethylamine (4.5 mL, 15.5 mmol) in EtOH (10 mL). The sealed tube was placed into the cavity of a focused monomode microwave reactor (CEM Discover) and irradiated in 100 W for 20 min at 80° C. The solvent was removed by rotary evaporation. The residue is purified by flash chromatography (silica gel, MeOH/EtOAc=1:9) to afford $N^5$-[(3-bromothien-2-yl) methyl]adenosine.

$N^6$-[(2-Bromothien-3-yl)methyl]adenosine

In a sealed tube (15 mL) was added (2-bromothien-3-yl) methanamine (384 mg, 2 mmol), 6-chloropurine ribofuranoside (287 mg, 1 mmol), and diisopropylethylamine (3 mL, 17 mmol) in EtOH (8 mL). The sealed tube was placed into the cavity of a focused monomode microwave reactor (CEM Discover) and irradiated in 100 W for 20 min at 80° C. The solvent was removed by rotary evaporation. The residue was purified by flash chromatography (silica gel, MeOH/ EtOAc=1:9) to afford $N^6$-[(2-bromothien-3-yl)methyl]adenosine.

$N^6$-[(4-Bromothien-3-yl)methyl]adenosine

A mixture of (4-bromothien-3-yl)methanamine (768 mg, 4 mmol), 6-chloropurine ribofuranoside (143 mg, 0.5 mmol), and diisopropylethylamine (2 mL, 12 mmol) in 1-propanol (20 mL) was heated at 70° C. for 7 h. The mixture containing the desired product and unreacted (4-bromothien-3-yl)methanamine was treated with di-tert-butyl dicarbonate (0.92 mL, 4 mmol) in THF (6 mL) and NaHCO$_3$ (672 mg, 8 mmol) at room temperature for 2 h. The mixture was concentrated by rotary evaporation and purified by flash chromatography (silica gel, MeOH/EtOAc=1:9) to afford $N^6$-[(4-bromothien-3-yl)methyl]adenosine.

6-N-(5-Bromothien-3-yl)methyl-6-N-tert-butoxycarbonyl-2',3'-O-isopropylidene-5'-O-(tert-butyldimethylsilyl)adenosine A solution of compound 6 (360 mg, 0.68 mmol), (5-bromothien-3-yl)methanol (197 mg, 1.02 mmol) and triphenylphosphine (271 mg, 1.02 mmol) in anhydrous THF (10 mL) was stirred at 45° C. for 2 min under an atmosphere of N$_2$. Diisopropyl azodicarboxylate (DIAD, 0.20 mL, 1.02 mmol) was added dropwise. The mixture was stirred until the TLC analysis showed disappearance of compound 6. The mixture was concentrated under reduced pressure by rotary evaporation. The crude product was purified by flash chromatography (EtOAc/hexane=1:9) to afford 6-N-(5-bromothien-3-yl)methyl-6-N-tert-butoxycarbonyl-2',3'-O-isopropylidene-5'-O)-(tert-butyldimethylsilyl)adenosine.

$N^6$-[(5-Bromothien-3-yl)methyl]adenosine

A suspension of 6-N-(5-bromothien-3-yl)methyl-6-N-tert-butoxycarbonyl-2',3'-O-isopropylidene-5'-O-(tert-butyldimethylsilyl)adenosine (138 mg, 0.19 mmol) in deionized water (5 mL) and THF (1 mL) was stirred and cooled in an ice bath. Trifluoroactetic acid (5 mL) was added dropwise at 0° C. The mixture was stirred for 10 min, the ice bath was removed, and the mixture was stirred for another 30 min. The mixture was concentrated under reduced pressure by rotary evaporation. The crude product was purified by flash chromatography (MeOH/EtOAc=1:49) to afford $N^6$-[(5-bromothien-3-yl)methyl]adenosine.

(5-Chlorothien-2-yl)methanamine

A mixture of 2-(aminomethyl)thiophene (1 mL, 10 mmol), di-tert-butyl dicarbonate (2.5 mL, 11 mmol), and NaHCO$_3$ (840 mg, 10 mmol) in THF (13 mL) was stirred at room temperature for 3 h to give a suspension containing pale yellow solids. The mixture was concentrated under reduced pressure, and the residue was extracted with CH$_2$Cl$_2$ and H$_2$O. The organic phase was dried over MgSO$_4$, filtered, and purified by flash chromatography on a silica gel column with elution of EtOAc/hexane (1:20) to give tert-butyl (thien-2-yl)methyl carbamate ($C_1H_{15}NO_2S$, 1.62 g, 76% yield).

A mixture of tert-butyl (thien-2-yl)methyl carbamate (106 mg, 0.5 mmol), N-chlorosuccinimide (73 mg, 0.55 mmol) in benzene (0.3 mL) was stirred at 80° C. After 2 h, acetic acid (0.3 mL, 5 mmol) was added and reacted for further 21 h. The mixture was extracted with CH$_2$Cl$_2$ and H$_2$O. The organic phase was dried over MgSO$_4$, filtered, and purified by flash chromatography on a silica gel column with elution of EtOAc/hexane (1:20) to give tert-butyl (5-chlorothien-2-yl)methyl carbamate ($C_{10}H_{14}ClNO_2S$, 82.6 mg, 67% yield).

A mixture of the above-prepared compound (65 mg, 0.26 mmol) and TFA (1 mL, 13 mmol) in $CH_2Cl_2$ (1 mL) was stirred for 3 h at room temperature. The solution was concentrated under reduced pressure to give (5-chlorothien-2-yl)methanamine (~100% yield). $C_5H_6NSCl$; pale yellow solid; $^1H$ NMR (400 MHz, $CD_2OD$) δ 7.07 (1 H, d, J=4.0 Hz), 6.95 (1 H, d, J=3.6 Hz), 4.26 (2 H, s); $^{13}C$ NMR (100 MHz, $CD_3OD$) δ 134.9, 132.8, 130.7, 128.0, 38.8; ESI-HRMS calcd for $C_5H_7ClNS$: 147.9988, found: m/z 147.9995 $[M+H]^+$.

$N^6$-[(5-Chlorothien-2-yl)methyl]adenosine (JMF3818)

A mixture of (5-chlorothien-2-yl)methanamine (35.4 mg, 0.24 mmol), 6-chloropurine ribofuranoside (0.12 mmol) and diisopropylethylamine (0.36 mL, 2 mmol) in EtOH (1 mL) was stirred in a seal tube at 80° C. by microwave irradiation for 30 min. The mixture was cooled to room temperature, and concentrated under reduced pressure to give pale yellow oil, which was washed successively with $H_2O$ and MeOH to give the title compound JMF3818. $C_{15}H_{16}ClN_5O_4S$; white solid; $^1H$ NMR (400 MHz, $CD_3OD$) δ 8.29 (1 H, s), 8.27 (1 H, s), 6.88 (1 H, d, J=3.6 Hz), 6.79 (1 H, d, J=3.6 Hz), 5.96 (1 H, d, J=6.8 Hz), 4.74-4.77 (1 H, m), 4.32-4.34 (1 H, m), 4.17 (1 H, d, J=2.8 Hz), 3.89 (1 H, dd, J=12.4, 2.0 Hz), 3.75 (1 H, dd, J=12.4, 2.8 Hz); $^{13}C$ NMR (100 MHz, $CD_3OD$) δ 156.0, 153.6, 142.8, 142.0, 129.9, 127.0, 126.6, 121.7, 91.5, 88.4, 75.6, 72.9, 63.7, 40.4; ESI-HRMS calcd for $C_{15}H_{17}ClN_5O_4S$: 398.0690, found: m/z 398.0692 $[M+H]^+$.

Pharmacokinetic Study. The compound was administered as aqueous solutions in normal saline. Male ICR mice were purchased from BioLASCO Taiwan Co., Ltd. To measure oral bioavailability of test compounds (T1-11 and JMF3464), blood samples were collected from male ICR mice (6 weeks old; 20-258 g) after oral (10 mg/kg) or intravenous (1 mg/kg) administrations of test compounds. For T1-11, blood samples were collected at 2, 10, 30, 60, 120, 360 minutes after intravenous administration and at 15, 30, 45, 60, 120, 360 minutes after oral administration. For JMF3464, the blood samples were collected at 2, 10, 30, 60, 120, 240, 360, 480 minutes after intravenous administration and at 15, 30, 60, 90, 120, 240, 360, 480 minutes after oral administration. The blood samples were extracted by methanol with 0.1% formic acid, and then 10 μL of the extracted samples were injected to UPLC-MSMS for quantitation.

The pharmacokinetic parameters were obtained using a pharmacokinetic program WinNonlin, fitting data to a non-compartmental model. The pharmacokinetic parameters including the area under the plasma concentration-versus-time curve (AUC) to the last sampling time, ($AUC_{0-120}$), to the time infinity ($AUC_{0-\infty}$), the terminal-phase half-life ($T_{1/2}$), the maximum concentration of compound in plasma ($C_{max}$), the time of $C_{max}$ ($T_{max}$), and the first order rate constant associated with the terminal portion of the curve (k) were estimated via linear regression of time vs. log concentration. The total plasma clearance (CL) was calculated as dose/$AUC_{i.v.}$. The oral bioavailability (F) of the test compound by oral administration was calculated from the $AUC_{0-\infty}$ of the oral dose divided by the $AUC_{0-\infty}$ of the i.v. dose.

EXAMPLE 2

Radioligand binding assays. Radioligand binding assays were performed by MDS Pharma Services Taiwan (Taipei, Taiwan) using standard binding protocols. For $A_{2A}R$ binding assays, membrane proteins collected from HEK293 cells overexpressing human $A_{2A}R$ were incubated in the reaction buffer [50 mM Tris-HCl (pH 7.4), 10 mM $MgCl_2$, 1 mM EDTA, and 2 U/mL adenosine deaminase] containing $^3H$-CGS21680 (50 nM) for 90 min at 25° C. Nonspecific binding was assessed in the presence of 50 μM adenosine-5'-N-ethylcarboxamide. To measure the binding affinity of T-11 to the $A_3R$, membrane proteins collected from Chinese hamster ovary (CHO)-K1 cells overexpressing human $A_3R$ were incubated with $^3H$-AB-MECA (0.5 nM) for 60 min at 25° C. in the reaction buffer containing 25 mM HEPES (pH 7.4), 5 mM $MgC_2$, 1 mM CaCl, and 0.1% bovine serum albumin. Nonspecific binding was assessed in the presence of 1 μM IB-MECA (Tocris Bioscience, Ellisville, Mo., USA). Binding assays for adenosine transporters were conducted as described earlier. Membrane fractions collected from the cerebral cortex of Duncan Hartley-derived guinea pigs were incubated with $^3H$-labeled 6-[(4-nitrobenzyl)thio]-9-β-D-ribofuranosylpurine (NBTI, 0.5 nM) for 30 min at 25° C. in the incubation buffer containing 50 mM Tris-HCl (pH 7.4). Nonspecific binding was assessed in the presence of 5 μM NBTI, an effective inhibitor of equilibrative nucleoside transporters. Note that NBTI is a high-affinity inhibitor of ENT1, and inhibits only human (h)ENT1 at 0.5 nM. Reactions were terminated by filtration over GF/B glass fibers and washing with the reaction buffer.

Cell Culture and Transient Transfection

Rat PC12 cells purchased from American Type Culture Collection (ATCC; Manassas, Va., USA) were maintained in DMEM supplemented with 10% horse serum and 5% FBS and incubated in a $CO_2$ incubator (5%) at 37° C. LIPOFECTAMINE™ 2000 (Invitrogen) was used as a vehicle to transfer plasmids into cells according to the manufacture's protocol. Plasmids were kindly provided by Dr. Pulst (Department of Neurology, University of Utah, USA). Normally, 5 μg of DNA combined with 5 μl of LIPOFECTAMINE™ 2000 was applied to each well of 6-well plates. The plating number was $(1\sim1.5)\times10^6$ cells/well. After transfections for 6 h, cells were treated with reagents for another 24 h. Images were taken with a Zeiss Axiovert 200M inverted fluorescence microscope (Göttingen, Germany).

MTT assay. Survival was assessed by 3-(4,5-dimethylthiazol-2-yl)-2,5-diphenyl tetrazolium bromide (MTT) metabolism assay. In brief, after treatment, MTT was added to the medium (0.5 mg/ml) and incubated at 37° C. for 2-3 h. The plating number was $1\times10^4$ cells/well in a 96-well plate. After discarding the medium, DMSO was applied to the well to dissolve formazan crystals, and the absorbances at 570 and 630 nm in each well were measured on a micro-enzyme-linked immunosorbent assay (ELISA) reader.

EXAMPLE 3

Animals and drug administration. Male R6/2 mice (Mangiarini et al., 1996 *Cell.* 87:493-506) and littermate controls were originally obtained from Jackson Laboratories (Bar Harbor, Me., USA), and mated to female control mice (B6CBAFI/J). Offspring were identified by a polymerase chain reaction (PCR) genotyping technique of genomic DNA extracted from tail tissues using primers located in the transgene (5'-CCGCTCAGGTTCTGCTTTTA-3'; SEQ ID NO: 1, and 5'-GGCTGAGGAAGCTGAGGAG-3'; SEQ ID NO: 2) to ensure that the number of CAG repeats remained approximately 150. Animals were housed at the Institute of Biomedical Sciences Animal Care Facility under a 12/12-h light/dark cycle. Body weights of mice were recorded once daily. Animal experiments were performed under protocols approved by the Academia Sinica Institutional Animal Care and Utilization Committee, Taipei, Taiwan.

Rotarod performance. Motor coordination was assessed using a rotarod apparatus (UGO BASILE, Comerio, Italy) at a constant speed (12 rpm) over a period of 2 min (Carter et al., 1999 *J Neurosci.* 19:3248-3257). All mice were trained for 2 days at the age of 4 weeks to allow them to become acquainted with the rotarod apparatus. Animals were then tested three times per week at the ages of 4~12 weeks. For each test, animals were placed in the apparatus before initiation of rotation. Latency to fall was recorded automatically. Each mouse was given three trials for a maximum of 2 min for each trial.

EXAMPLE 4

Animals. The C57BL/6 mice were purchased from National Laboratory Animal Center (Taiwan). The transgenic mice (ATAXN2$^{Q127}$) were provided by Dr. Pulst. Mice were kept in a soundproof room under a 12/12 h light/dark cycle and controlled temperature (22±2° C.). Food and water were available ad libitum. All efforts were made to minimize the number of animals used and their pain and discomfort, according to the principles and directives of the NIH Guide for the Care and Use of Laboratory Animals. These experiments were also reviewed and approved by the Institutional Animal Care and Use Committee at the National Research Institute of Chinese Medicine (Approval No: 100-15).

Filter retardation assay. This method followed that described by Wanker et al. (1999 *Methods Enzymol.* 309: 375-386) with a few modifications. In brief, harvested cells were resuspended in the lysis buffer (50 mM Tris-HCl (pH 8.8), 100 mM NaCl, 5.0 mM $MgCl_2$, 1 mM EDTA, and 0.5% (w/v) IPGEAL containing 1× protease inhibitor cocktail (Roche Diagnostics, Indianapolis, Ind., USA)) and sonicated for 10 s (1 pulse/s). Equal protein concentrations (15~20 µg/well) in each group were filtered through a 2% sodium dodecylsulfate (SDS)-pre-equilibrated cellulose-acetate membrane (0.2 µm; Whatman, Maidstone, Kent, UK) using the Bio-Dot SF Apparatus (Bio-Rad, Hercules, Calif., USA). During suction, each well was washed with 200 µl 0.1% SDS twice. The blot was blocked in TBS (100 mM Tris-HCl and 150 mM NaCl; pH 7.4) containing 3% nonfat dried milk for 1 h at room temperature and then incubated with anti-polyglutamine (1:5000; MAB1574) antibody in 3% bovine serum albumin (BSA) with 0.02% $NaN_3$ (4° C. overnight) to probe normal and mutant ATAXN2. The subsequent methods were the same as those described above.

Rotarod performance. The wild type and transgenic mice at the age of 5 weeks old were used in this study. Motor coordination was assessed using a rotarod apparatus (UGO BASILE, Comerio, Italy) at an accelerated speed (10 to 28 rpm) over a period of 5 min. All mice were trained for 2 days within the age of 5 weeks to allow them to become acquainted with the rotarod apparatus. Besides, in this week part of the transgenic mice were started to take T1-11 dissolving in their daily drinking water. Animals were then formally tested 2 times per week from the age of 6 weeks. For each test, animals were placed in the apparatus before initiation of rotation. Latency to fall was automatically recorded. Each mouse was given 2 trials per time. Mice were permitted to rest for 20-30 min between trials.

EXAMPLE 5

Behavioral test. Balance and coordination functions of mice were determined by performing rotarod test. Mice were placed on the moving drum of a rotarod apparatus (Accelerating Model, Ugo Basile Biological Research Apparatus), which was then accelerated until mouse fell from the drum onto a plate to stop the timer. Latency to fall was measured in four daily trials over the course of 4 days.

Immunohistochemical staining. Wild-type or SCA3 transgenic mice were anesthetized and perfused transcardially with 4% paraformaldehyde in PBS. Brain was equilibrated in Tissue-Tek embedding medium and frozen in liquid nitrogen. Coronal sections (20 µm) prepared by cryostat sectioning were permeabilized in 0.1% Triton X-100, and incubated at 4° C. for 48 hours with diluted anti-NeuN monoclonal antiserum (Chemicon). Subsequently, sections were washed and incubated with biotinylated horse anti-mouse IgG followed by incubation with avidin-biotin-horseradish peroxidase complex. The sections were then washed and developed in a diaminobenzidine solution. NeuN-positive neurons were visualized and counted by a Leica DM2500 microscope equipped with a Retiga-2000R CCD camera (QImaging) and a 3-axis computer-controlled MAC 600 motorized stage (Ludl Electronics) with the aid of StereoInvestigator software (MBF Bioscience). Each analysis included the processing of 15 brain sections per mouse.

EXAMPLE 6

Animals and drug delivery. Transgenic mice B6SJL-Tg (Prnp-TARDBP)4Jlel/J were purchased from the Jackson Laboratory (Bar Harbor, Me. USA), and bred by the National Laboratory Animal Center in Tainan. The transgenic mice were screened by PCR with a forward primer 5'-GGT GGT GGG ATG AAC TTT GG-3' (SEQ ID NO: 3) and a reverse primer 5'-GTG GAT AAC CCC TCC CCC AGC CTA GAC-3' (SEQ ID NO: 4). The wild type mice were non-transgenic littermates. Mice of 6 weeks of age received surgery to bear an ALZET micro-osmotic pump Model 1004 (DURECT Corporation, Cupertino, Calif., USA) containing DMSO or JMF1907 as indicated, embedded subcutaneously at the ventral lateral side of the abdomen. The pump was replaced every 28 days.

Grip strength. The grip strength was measured with Grip Strength-Meter (TSE Systems, Inc., MO, USA). Briefly, a mouse was hand-picked by its tail and allowed to grasp a height-adjustable grip mounted on a force sensor. A pulling force was applied to the mouse by its tail. The maximum force was shown on a digital display panel of a connected control unit when the mouse released its grip. Each mouse was repeatedly tested 3 times.

Rotarod performance. The motor coordination of wild type and transgenic mice was assessed using an apparatus (UGO BASILE, Comerio, Italy) at constant speed (40 rpm) for 120 seconds. All mice were trained for 2 days per week for 2 weeks. Mice were then formally tested 2 times per week from the age of 9 weeks. For each test, animals were placed in the apparatus before initiation of rotation. Latency to fall was automatically recorded. Each mouse was given 3 trials per time. Mice were permitted to rest for 20 min between trials.

Cell culture and transfection. The motor neuron cell line (NSC34) was a generous gift from Dr. Neil Cashman (Brain Research Centre, The University of British Columbia, Canada), and cultured in a high-glucose Dulbecco's modified Eagle's medium (DMEM) containing 10% fetal calf serum (FCS), 2 mM L-glutamine, and 1% penicillin/streptomycin (Invitrogen GibcoBRL, Carlsbad, Calif., USA) at 37° C. under 5% $CO_2$.

EXAMPLE 7

Mice. Female C57BL6N mice aged 8-12 weeks were purchased from BioLASCO (Yi-Lan, Taiwan).

Acid-induced chronic widespread pain model. The fibromyalgia model was modified from the acid-induced chronic pain model established by Sluka's group (Sluka et al., 2003 *Pain.* 106:229-239).

Mice were briefly anesthetized with 2% vaporized isoflurane and received an i.m. injection of 20 µL genistein (1 µM) in the left gastrocnemius muscle. After 3 minutes, an injection of 20 µL acid saline (pH 4.0) was given to the same site. The mice then developed long-lasting mechanical hyperalgesia for more than 2 weeks. Analgesic effects of T1-11 (p.o. with an 0.9-mm/7-cm gavage) were tested 4 days after mice had developed the mechanical hyperalgesia. Mechanical hyperalgesia was assayed by testing the withdrawal response of mouse hindpaws to 0.2-mN von Frey filament stimulation.

Intermittent cold stress model. The fibromyalgia model was developed by Ueda's group, in which mice were treated with intermittent cold stress for 2 days (Nishiyori and Ueda, 2008 *Mol Pain.* 4:52). Mice treated with intermittent cold stress developed long-lasting (>2 weeks) mechanical and thermal hyperalgesia. Analgesic effects of JMF3464 (i.p. or p.o.) were tested in these mice 5 days after intermittent cold stress. Mechanical hyperalgesia was assayed by testing the withdrawal response of mouse hindpaws to 0.2-mN von Frey filament stimulation.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope.

All references cited and discussed in this specification are incorporated herein by reference in their entireties and to the same extent as if each reference was individually incorporated by reference.

What is claimed is:

1. A compound of formula (I) or (IA):

or a pharmaceutically acceptable salt thereof, wherein X is halogen.

2. The compound of claim 1, which is selected from the group consisting of $N^6$-[(3-halothien-2-yl)methyl]adenosine, $N^6$-[(4-halothien-2-yl)methyl]adenosine, and $N^6$-[(5-halothien-2-yl)methyl]adenosine.

3. The compound of claim 2, which is selected from the group consisting of $N^6$-[(5-bromothien-2-yl)methyl]adenosine, $N^6$-[(4-bromothien-2-yl)methyl]adenosine, $N^6$-[(3-bromothien-2-yl)methyl]adenosine, $N^6$-[(5-chlorothien-2-yl)methyl]adenosine, $N^6$-[(4-chlorothien-2-yl)methyl]adenosine, and $N^6$-[(3-chlorothien-2-yl)methyl]adenosine.

4. The compound of claim 1, which is selected from the group consisting of $N^6$-[(2-halothien-3-yl)methyl]adenosine, $N^6$-[(4-halothien-3-yl)methyl]adenosine, and $N^6$-[(5-halothien-3-yl)methyl]adenosine.

5. The compound of claim 4, which is selected from the group consisting of $N^6$-[(2-bromothien-3-yl)methyl]adenosine, $N^6$-[(4-bromothien-3-yl)methyl]adenosine, $N^6$-[(5-bromothien-3-yl)methyl]adenosine $N^6$-[(2-chlorothien-3-yl)methyl]adenosine, $N^6$-[(4-chlorothien-3-yl)methyl]adenosine, and $N^6$-[(5-chlorothien-3-yl)methyl]adenosine.

6. A method for preparing a compound of formula (I) or (IA) claim 1, comprising the step of (I) or (II):
(I)
(a) reacting 6-chloropurine ribofuranoside in the presence of a base with substituted (thienyl)methanamine having a formula 3 or 3A:

wherein X is fluorine, chlorine, bromine or iodine, to afford the compound of formula (I) or (IA); or
(II)
(a1) reacting (2′,3′-O-isopropylidene)adenine in the presence of a base with a hydroxyl group-protecting agent to afford a derivative of (2′,3′-O-isopropylidene)adenine having a hydroxyl protecting group;
(b) reacting the derivative of (2′,3′-O-isopropylidene)adenine having the hydroxyl protecting group with an amine group-protecting agent to afford a derivative of (2′,3′-O-isopropylidene)adenine having the hydroxyl protecting group and an amine protecting group;
(c) performing a coupling reaction by reacting the derivative of (2′,3′-O-isopropylidene)adenine having the hydroxyl and amine protecting groups with a substituted (thienyl)methyl group-containing compound of formula 7 or 7A:

wherein X is F, Cl, Br, or I, and Y is X, OH, methanesulfonate ($OSO_2CH_3$, OMs), p-toluenesulfonate ($OSO_2C_6H_4$-p-$CH_3$, OTs), or trifluoromethanesulfonate ($OSO_2CF_3$, OTf),
to afford a product containing the protecting groups and the substituted (thienyl)methyl group; and
(d) removing the protecting groups from the product of step (II)(c) in an acidic condition to afford the compound of formula (I) or (IA).

7. The method of claim 6, wherein in step (I)(a) the base is diisopropylethylamine and the substituted (thienyl)methanamine is:
(i)(5-bromothien-2-yl)methanamine to afford $N^6$-[(5-bromothien-2-yl)methyl]adenosine; or
(ii)(5-chlorothien-2-yl)methanamine to afford $N^6$-[(5-chlorothien-2-yl)methyl]adenosine.

8. The method of claim 6, wherein in step (II)(c) the coupling reaction is preformed in the presence of triphenylphosphine and diisopropyl azodicarboxylate.

9. The method of claim 8, wherein in step (II)(c) the substituted (thienyl)methyl group-containing compound is (5-bromothien-2-yl)methanol.

10. A composition comprising:
(a) a therapeutically effective amount of a compound of claim 1 or a pharmaceutically acceptable salt thereof; and
(b) a pharmaceutically acceptable carrier, excipient or vehicle.

11. A method for treating a neurodegenerative disease and/or pain in a subject in need thereof, comprising administering to the subject a therapeutically effective amount of a compound of claim 1.

12. The method of claim 11, wherein the neurodegenerative disease is selected from the group consisting of Alzheimer's disease, Parkinson's disease, amyotrophic lateral sclerosis, Prion disease, Huntington's disease, and spinal cerebellar ataxias.

13. The method of claim 12, wherein the spinal cerebellar ataxias is selected from the group consisting of spinal cerebellar ataxias 2, spinal cerebellar ataxias 3, and spinal cerebellar ataxias 7.

14. The method of claim 11, wherein the pain is acid-induced pain.

15. The method of claim 14, wherein the acid-induced pain is acid-induced muscle pain.

16. The method of claim 15, wherein the acid-induced muscle pain is acid-induced chronic muscle pain.

17. The method of claim 11, wherein the pain is dysfunctional pain.

18. The method of claim 17, wherein the dysfunctional pain is selected from the group consisting of fibromyalgia, myofascial pain, bladder pain syndrome, and pain caused by irritable bowel syndrome.

19. The method of claim 11, wherein the pain is selected from the group consisting of inflammatory pain, cancer pain, chest pain, back pain, neck pain, shoulder pain, migraine, headache, myofascial pain, join pain, muscular pain syndromes, neuropathic pain, peripheral pain, sympathetic pain, postoperative pain, post-traumatic pain, and multiple sclerosis pain.

20. The method of claim 11, wherein the neurodegenerative disease is a protein-misfolding disease.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Forward primer for CAG repeats

<400> SEQUENCE: 1
ccgctcaggt tctgctttta                                              20

<210> SEQ ID NO 2
<211> LENGTH: 19
<212> TYPE: DNA
<213> ORGANISM: Artificial Sequence
<220> FEATURE:
<223> OTHER INFORMATION: Reverse primer for CAG repeats

<400> SEQUENCE: 2
ggctgaggaa gctgaggag                                               19

<210> SEQ ID NO 3
<211> LENGTH: 20
<212> TYPE: DNA
<213> ORGANISM: Artificial Sequence
<220> FEATURE:
<223> OTHER INFORMATION: Forward primer for transgene Prnp-TARDBP

<400> SEQUENCE: 3
ggtggtggga tgaactttgg                                              20

<210> SEQ ID NO 4
<211> LENGTH: 27
<212> TYPE: DNA
<213> ORGANISM: Artificial Sequence
<220> FEATURE:
<223> OTHER INFORMATION: Reverse primer for transgene Prnp-TARDBP

<400> SEQUENCE: 4
gtggataacc cctcccccag cctagac                                      27
```